United States Patent [19]
Luria et al.

[11] Patent Number: 6,013,437
[45] Date of Patent: Jan. 11, 2000

[54] METHOD FOR IDENTIFYING TRANSLATIONALLY REGULATED GENES

[75] Inventors: Sylvie Luria; Paz Einat, both of Nes-Ziona; Nicholas Harris, Rehovot; Rami Skaliter, Nes-Ziona; Zehava Grosman, Rehovot, all of Israel

[73] Assignee: QBI Enterprises, Ltd., Israel

[21] Appl. No.: 08/748,130

[22] Filed: Nov. 12, 1996

[51] Int. Cl.[7] .................................................. C12Q 1/68
[52] U.S. Cl. ................... 435/6; 435/5; 435/91.1; 435/91.3; 435/287.2
[58] Field of Search .................. 435/5, 6, 91.1, 435/91.3, 287.2; 536/24.33

[56] References Cited

U.S. PATENT DOCUMENTS 5,459,037 10/1995 Sutcliffe et al. ............................ 435/6
5,525,471 6/1996 Zeng ............................................ 435/6

*Primary Examiner*—Laurie Scheiner
*Attorney, Agent, or Firm*—Kohn & Associates

[57] ABSTRACT

A method for identifying translationally regulated genes includes selectively stimulating translation of an unknown target mRNA with a stress inducing element wherein the target mRNA is part of a larger sample of mRNA. The mRNA sample is divided into pools of translated and untranslated mRNA which are differentially analyzed to identify genes that are translationally regulated by the stress inducing element. A method for identifying gene sequences coding for internal ribosome entry sites includes inhibiting 5' cap-dependant mRNA translation in a cell, collecting a pool of mRNA from the cells, and differentially analyzing the pool of mRNA to identify genes with sequences coding for internal ribosome entry sites.

20 Claims, 6 Drawing Sheets

SEQUENCE LISTING

```
(1) GENERAL INFORMATION:

(iii) NUMBER OF SEQUENCES: 29

(2) INFORMATION FOR SEQ ID NO:1:

(i) SEQUENCE CHARACTERISTICS:
         (A) LENGTH: 30 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "Primer"

(xi) SEQUENCE DESCRIPTION: SEQ ID NO:1:

CATTATGCTG AGTGATATCT TTTTTTTTVV                                              30

(2) INFORMATION FOR SEQ ID NO:2:

(i) SEQUENCE CHARACTERISTICS:
         (A) LENGTH: 30 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "Primer"

(xi) SEQUENCE DESCRIPTION: SEQ ID NO:2:

CATTATGCTG AGTGATATCT TTTTTTTTAA                                              30

(2) INFORMATION FOR SEQ ID NO:3:

(i) SEQUENCE CHARACTERISTICS:
         (A) LENGTH: 30 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "primer"

(xi) SEQUENCE DESCRIPTION: SEQ ID NO:3:

CATTATGCTG AGTGATATCT TTTTTTTAC                                               30
```

(2) INFORMATION FOR SEQ ID NO:4:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:4:

CATTATGCTG AGTGATATCT TTTTTTTTAG        30

(2) INFORMATION FOR SEQ ID NO:5:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:5:

CATTATGCTG AGTGATATCT TTTTTTTTCA        30

(2) INFORMATION FOR SEQ ID NO:6:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:6:

CATTATGCTG AGTGATATCT TTTTTTTTCC        30

(2) INFORMATION FOR SEQ ID NO:7:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:7:

CATTATGCTG AGTGATATCT TTTTTTTTCG        30

(2) INFORMATION FOR SEQ ID NO:8:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:8:

CATTATGCTG AGTGATATCT TTTTTTTTGA        30

(2) INFORMATION FOR SEQ ID NO:9:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:9:

CATTATGCTG AGTGATATCT TTTTTTTTGC          30

(2) INFORMATION FOR SEQ ID NO:10:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:10:

CATTATGCTG AGTGATATCT TTTTTTTTGG          30

(2) INFORMATION FOR SEQ ID NO:11:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:11:

ATTAACCCTC ACTAAANNNN NNNNNN            26

(2) INFORMATION FOR SEQ ID NO:12:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:12:

ATTAACCCTC ACTAAATGCT GGGGA              25

(2) INFORMATION FOR SEQ ID NO:13:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:13:

ATTAACCCTC ACTAAATGCT GGAGG              25

(2) INFORMATION FOR SEQ ID NO:14:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:14:

ATTAACCCTC ACTAAATGCT GGTAG                              25

(2) INFORMATION FOR SEQ ID NO:15:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:15:

ATTAACCCTC ACTAAATGCT GGTAG                              25

(2) INFORMATION FOR SEQ ID NO:16:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:16:

ATTAACCCTC ACTAAAGATC TGACTG                            26

(2) INFORMATION FOR SEQ ID NO:17:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:17:

ATTAACCCTC ACTAAATGCT GGGTG                              25

(2) INFORMATION FOR SEQ ID NO:18:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:18:

ATTAACCCTC ACTAAATGCT GTATG                              25

(2) INFORMATION FOR SEQ ID NO:19:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:19:

ATTAACCCTC ACTAAATGGA GCTGG                              25

(2) INFORMATION FOR SEQ ID NO:20:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:20:

ATTAACCCTC ACTAAATGTG GCAGG                              25

(2) INFORMATION FOR SEQ ID NO:21:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:21:

ATTAACCCTC ACTAAATGCA CCGTCC                             26

(2) INFORMATION FOR SEQ ID NO:22:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:22:

GATCTGCGGT GA                                                  12

(2) INFORMATION FOR SEQ ID NO:23:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:23:

AGCACTCTCC AGCCTCTCAC CGCA                               24

(2) INFORMATION FOR SEQ ID NO:24:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:24:

GATCTGTTCA TG                                                                 12

(2) INFORMATION FOR SEQ ID NO:25:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:25:

ACCGACGTCG ACTATCCATG AACA                                    24

(2) INFORMATION FOR SEQ ID NO:26:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:26:

GATCTTCCCT CG                                                                 12

(2) INFORMATION FOR SEQ ID NO:27:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:27:

AGGCAACTGT GCTATCCGAG GGAA                                    24

(2) INFORMATION FOR SEQ ID NO:28:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:28:

GCAACTACCA TTTGGCCACT CAGGAAG                                  27

(2) INFORMATION FOR SEQ ID NO:29:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:29:

GCAACCAACC CTTCTCCACC AGCAG                  25

METHOD FOR IDENTIFYING TRANSLATIONALLY REGULATED GENES

BACKGROUND OF THE INVENTION

1. Technical Field

The present invention relates to a method for identifying genes that are translationally regulated. More specifically, the present invention relates to the rapid isolation of differentially expressed or developmentally regulated gene sequences through segregation of mRNAs into translated and untranslated pools and comparing the relative abundance of the mRNAs found in these pools by differential analysis.

2. Background Art

The identification and/or isolation of genes whose expression differs between two cell or tissue types, or between cells or tissues exposed to stress conditions, chemical compounds or pathogens, is critical to the understanding of mechanisms which underlie various physiological conditions, disorders, or diseases. Regulation of gene expression has been shown to play an important part in many biological processes including embryogenesis, aging, tissue repair, and neoplastic transformation. Gene regulation at the level of translation has been shown to be of critical importance. For example, it has been demonstrated that a group of mRNAs are stored in an egg as a pool of untranslated mRNAs which, following fertilization, shift into the pool of translated mRNAs. Another example of a change in the translational state of mRNA is a subgroup of mRNAs which code for heat shock proteins which are not translated under normal physiological conditions. These mRNAs begin to be translated following exposure of cells to high temperatures.

A number of methods have been developed for the detection and isolation of genes which are activated or repressed in response to developmental, physiological, pharmacological, or other cued events. One particular method is described in U.S. Pat. No. 5,525,471 to Zeng, is subtractive hybridization. Subtractive hybridization is a particularly useful method for selectively cloning sequences present in one DNA or RNA population but absent in another. The selective cloning is accomplished by generating single stranded complementary DNA libraries from both control cells/tissue (driver cDNA) and cell/tissue during or after a specific change or response being studied (tester cDNA). The two cDNA libraries are denatured and hybridized to each other resulting in duplex formation between the driver and tester cDNA strands. In this method, common sequences are removed and the remaining non-hybridized single-stranded DNA is enriched for sequences present in the experimental cell/tissue which is related to the particular change or event being studied. (Davis et al., 1987).

Currently used methodologies to identify mRNAs encoding proteins which are being induced/reduced following a cue or stimulus rely on changes in the mRNA levels following transcriptional induction/repression via screening of differentially expressed mRNAs. One such method for the identification of differentially expressed mRNAs is disclosed in U.S. Pat. No. 5,459,037 to Sutcliffe et al. According to this method, an mRNA population is isolated, double-stranded cDNAs are prepared from the mRNA population using a mixture of twelve anchor primers, the cDNAs are cleaved with two restriction endonucleases, and then inserted into a vector in such an orientation that they are anti-sense with respect to a T3 promotor within the vector. *E. coli* are transformed with the cDNA containing vectors, linearized fragments are generated from the cloned inserts by digestion with at least one restriction endonuclease that is different from the first and second restriction endonucleouseases and a cDNA preparation of the anti-sense cDNA transcripts is generated by incubating the linearized fragments with a T3 RNA polymerase. The cDNA population is divided into subpools and the first strand cDNA from each subpool is transcribed using a thermostable reverse transcriptase and one of sixteen primers. The transcription product of each of the sixteen reaction pools is used as a template for a polymerase chain reaction (PCR) with a 3'-primer and a 5'-primer and the polymerase chain reaction amplified fragments are resolved by electrophoresis to display bands representing the 3'-ends of the mRNAs present in the sample. This method is useful for the identification of differentially expressed mRNAs and the measurement of their relative concentrations. This type of methodology, however, is unable to identify mRNAs whose levels remain constant but their translatability is variable or changes.

Schena et al. developed a high capacity system to monitor the expression of many genes in parallel utilizing microarrays. The microarrays are prepared by high speed robotic printing of cDNAs on glass providing quantitative expression measurements of the corresponding genes (Schena et al., 1995). Differential expression measurements of genes are made by means of simultaneous, two color fluorescence hybridization. However, this method alone is insufficient for the identification of translationally regulated genes.

The use of a known inhibitor of hypusine formation, mimosime, was used to reversibly suppress the hypusine-forming deoxyhypusyl hydroxylase in cells while differentially displaying their polysomal versus non-polysomal mRNA populations. (Hanauske-Abel et al., 1995) Utilizing this method, several species of mRNA were discovered which disappear and reappear, respectively, at polysomes in connection with inhibition and disinhibition of hypusine formation and which are thought to code for translationally controlled enzymes. This method only teaches the use of a known stimulating element (i.e., inducer or repressor) to identify translationally regulated genes. This method does not provide a mechanism for the detection and/or identification of translationally regulated genes where the stimulating element is unknown.

Generally, the translation of eukaryotic mRNAs is dependent upon 5' cap-mediated ribosome binding. Prior to translation, the ribosome small sub-unit (40S) binds to the 5'-cap structure on a transcript and then proceeds to scan along the mRNA molecule to the translation initiation site where the large sub-unit (60S) forms the complete ribosome initiation site. In most instances, the translation initiation site is the first AUG codon. This "scanning model" of translation initiation accommodates most eukaryotic mRNAs. A few notable exceptions to the "scanning model" are provided by the Picornavirus family. These viruses produce non-capped transcripts with long (600–1200 nucleotides) 5'-untranslated regions (UTR) which contain multiple non-translation initiating AUG codons. Because of the absence of a cap structure, the translational efficiency of these RNAs is dependent upon the presence of specific sequences within the untranslated regions (UTR) known as internal ribosome entry sites (IRES).

More recently, IRES containing mRNA transcripts have been discovered in non-viral systems such as the mRNA encoding for immunoglobulin heavy chain binding protein, the antenapedia gene in Drosophila, and the mouse Fg1-2 gene. These discoveries have promoted speculation for the role of cap-independent translation in the developmental regulation of gene expression during both normal and abnormal processes.

The discovery of the above-mentioned non-viral IRES containing mRNAs implies that eukaryotic IRES sequences could be more wide spread than has been previously realized. The difficulty in identifying eukaryotic IRES sequences resides in the fact that they typically cannot be identified by sequence homology. [Oh et al., 1993; Mountford et al., 1995; Macejak et al., 1991; Pelletier et al., 1988; Vagner et al. 1995] It would, therefore, be advantageous to have a method for identifying IRES containing mRNA in order to identify translationally controlled genes operating via 5'-cap independent translation in order to ascertain and assess their association with both normal and abnormal processes.

Therefore, it would be desirable to have a rapid, reliable, and reproducible method for the identification and cloning of clinically and therapeutically relevant differentially expressed genes which will overcome the inherent problems associated with the prior art methods.

SUMMARY OF THE INVENTION AND ADVANTAGES

According to the present invention, there is provided a method for identifying translationally regulated genes including the steps of selectively stimulating translation of an unknown target mRNA with a stress inducing element, the target mRNA being part of a larger sample of mRNA, dividing the sample of mRNA into pools of translated and untranslated mRNA and differentially analyzing the pools of mRNA to identify genes translationally regulated by the stress inducing element. Also, in accordance with the present invention, there is provided a method for identifying gene sequences coding for internal ribosome entry sites. The method includes inhibiting 5' cap-dependant mRNA translation in a cell, collecting a pool of mRNA from the cells, and differentially analyzing the pool of mRNA to identify genes with sequences coding for internal ribosome entry sites.

BRIEF DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE INVENTION

Figure 1A:
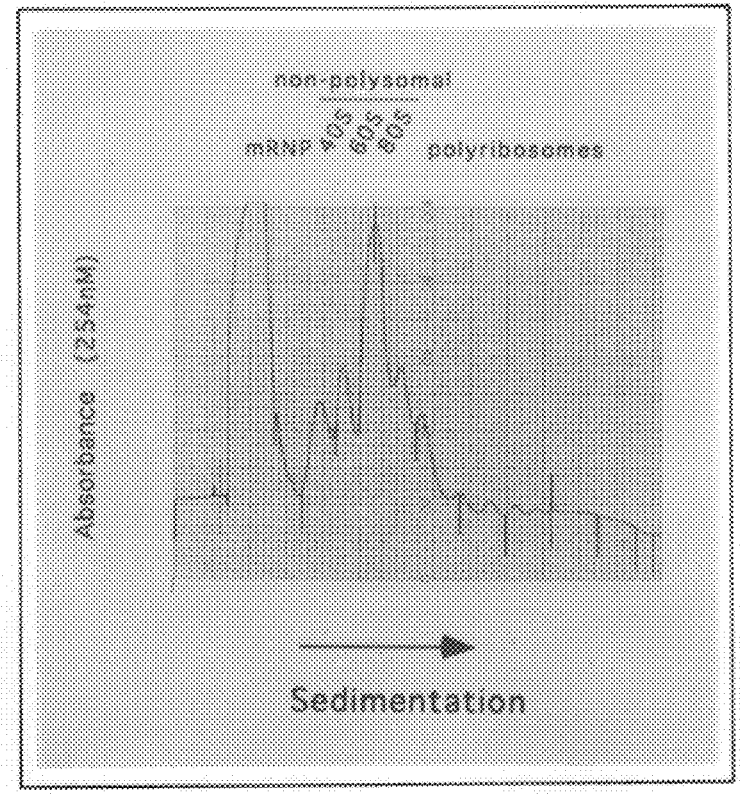
FIG. 1A is an absorbance profile of a fractionation of cytoplasmic RNA on a sucrose density gradient wherein the absorbance (at 254 nm) is plotted against the sedimentation rate of the cytoplasmic RNA.

The present invention provides a method for identifying translationally regulated genes by selectively stimulating translation of an unknown target mRNA with a stress inducing element, the target mRNA being part of a larger sample. The mRNA sample is divided into pools of translated and untranslated mRNA which are differentially analyzed to identify genes which are translationally regulated by the stress inducing element. This method is primarily designed for identifying and cloning genes which are regulated at the translational level. That is, the present method is designed for identifying and cloning genes which are either up- or down-regulated. The method of the present invention provides a novel approach to the identification and cloning of genes that are involved in fundamental cellular functions and which are regulated at the level of translation. The basic underlying theory for this method relies on the assumption that an mRNA encoding a protein required for a quick response to an external cue is generally stored as an untranslated mRNA. Following the appropriate external cue, the mRNA is translated and the encoded protein quickly appears. By comparing mRNA populations that are "active" or "non-active" at a given time, genes that are regulated by a mechanism referred to as the "shift mechanism" can be identified.

As used herein, RNA refers to RNA isolated from cells or tissues which are stimulated, differentiated, exposed to a chemical compound, are infected with a pathogen or otherwise stimulated. As used herein, translation is defined as the synthesis of protein on an mRNA template.

As used herein, the term stimulating translation of unknown target mRNA or stimulating element includes chemically, pathogenically, physically, or otherwise inducing or repressing an mRNA population from genes which can be derived from native tissues and/or cells under pathological/stress conditions that are regulated by the "shift mechanism." In other words, stimulating the translation of mRNA with a stress inducing element or "stressor" can include the application of an external cue, stimulus, or stimuli which stimulates or initiates translation of an untranslated mRNA stored as untranslated mRNA in the cell/tissue sample. In addition to stimulating translation of mRNA from genes in native cells/tissues, stimulation can include induction and/or repression of genes under pathological/stress conditions. The present method utilizes a stimulus or stressor to identify unknown target genes which are translationally regulated by the stress inducing element or stressor.

The method of the present invention integrates two previously known methodologies which were otherwise used separately. The first method is the division of an mRNA pool into separate translated and untranslated pools of mRNA. The second methodology involves the simultaneous comparison of the relative abundance of the mRNA species found in the separate pools by a methods of differential analysis such as differential display, representational difference analysis (RDA), gene expression microarray (GEM), or suppressive subtraction hybridization (SSH) (Diatchenko et al., 1996).

The specific cells/tissues which are to be analyzed in order to identify translationally regulated genes, can include any suitable cells and/or tissues. Any cell type or tissue can be used.

The cells/tissues to be analyzed under the present method are selectively stimulated utilizing a physiological, chemical, or pathological stress inducing element or stressor. In order to stimulate the translation of mRNA within the sample tissue. Following the stimulation of the translation of RNA, the RNA from the cells/tissues is isolated or extracted from the cells/tissues. The isolation of the RNA can be performed utilizing techniques which are well known to those skilled in the art and are described, for example, in "Molecular Cloning; A Laboratory Manual" (Cold Springs Harbor Laboratory Press, Cold Spring Harbor, N.Y., 1989). Other methods for the isolation and extraction of RNA from cells/tissue can be used and will be known to those of ordinary skill in the art. (Mach et al., 1986, Jefferies et al., 1994).

Following the isolation of the pool of translated and untranslated mRNA, the mRNAs which are actively engaged in translation and those which remain untranslated can be separated utilizing a procedure such as fractionation on a sucrose density gradient, high performance gel filtration chromatography, or polyacrylamide gel matrix separation (Ogishima et al., 1984, Menaker et al., 1974, Hirama et al., 1986, Mechler, 1987, and Bharucha and Murthy, 1992), since mRNAs that are being translated are loaded with ribosomes and, therefore, will migrate differently on a density gradient than ribosome-free untranslated mRNAs. By comparing mRNA populations that are active or non-active in translation at a given time, genes that are regulated by the "shift mechanism" can be identified.

Polysomal fractionation and specific analysis can be facilitated by treatment of target cell/tissue with drugs that will specifically inhibit or modulate transcription or translation. Examples of such drugs are actinomycin D and cyclohexamide, respectively.

The fractionation can be completed to create polysomal subdivisions. The subdivisions can be made to discriminate between total polyribosomes or membrane bound ribosomes by methods known in the art (Mechler, 1987).

Following isolation and division of the total mRNA population into separate translated and untranslated pools of mRNA, the relative abundance of the many mRNA species found in these pools are simultaneously compared using a differential analysis technique such as differential display, representational difference analysis (RDA), GEM-Gene Expression Microarrays. (Schena et al., 1995, Aiello et al., 1994, Shen et al., 1995, Bauer et al., 1993, Liang and Pardee, 1992, Liang and Pardee, 1995, Liang et al., 1993, Braun et al., 1995, Hubank and Schatz, 1994) and suppressive subtraction hybridization (SSH). The RNA isolated from the fractions can be further purified into mRNA without the ribosomal RNA by poly A selection.

Labeled mRNA (in a cDNA or PCR product form) from polysomal, non-polysomal or mRNPs (pools or individual fractions) can be used as probes, to identify clones of cDNA, genomic clones, and mRNA species that are fixed onto a solid matrix like microarrays (GEM), and membranes of any kind where clones can be either blotted after electrophoresis or directly loaded (dot blot) onto the membrane. The label can be radioactive, fluorescent, or incorporating a modified base such as digoxigenin and biotin.

Comparison between the fractions derived from the polyribosomal fraction to the total unfractionated material is essential to discriminate between differentials in expression levels that are result of transcription modulation from those that result from modulation of translation per se.

The present method for identifying translationally regulated genes is not limited by the source of the mRNA pools. Therefore, the present method can be utilized to clone genes from native cells/tissue under pathological/stress conditions that are regulated by the "shift mechanism," as well as genes that are induced/repressed under pathological/stress conditions. Following analysis by the selected method of differential analysis, the genes which have been identified as being regulated by translation can be cloned by any suitable cloning methodologies known to those skilled in the art. (Lisitsyn and Wigler, 1993).

Figure 1B:
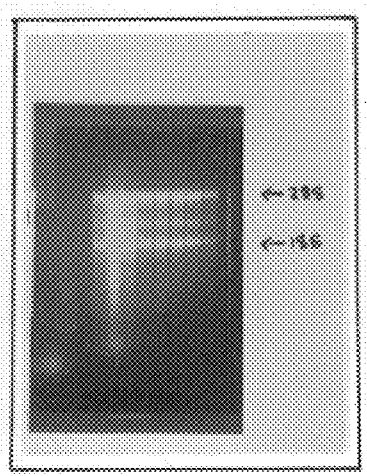
FIG. 1B is a photograph of purified RNA electrophoresed on an agarous gel and stained with ethidium bromide illustrating the fractionation of RNA.

Differential comparisons can be made of all possible permutations of polysomal vs. non-polysomal RNA where the definition of the fraction type is done, for example, by absorbance profile at 254 nm, density of the sucrose gradient as shown in FIG. 1A (or another size standard if high pressure liquid chromatography or gel systems are used) and types of RNA that are stained with ethidium bromide after electrophoresis of the fractions on agarous gels are completed, as shown in FIG. 1B. In FIG. 1A, the polysomal fractions are those that have mRNA with more than two ribosomes loaded. The materials and methods for this comparison are set forth below in the experimental section.

Differential comparisons can also include polysomal vs. non-polysomal fractions in each condition. By "condition" it is meant that cells from the same source, such as a cell line, a primary cell, or a tissue that undergoes different treatment or has been modified to have different features or to express different sets of genes. For example, this can be accomplished by differentiation, transformation, application of the stress such as oxygen deprivation, chemical treatment, or radiation. Permutations can include, for example:

1. polysomal fractions between conditions individually (migrating in the same density) or in a pool;
2. non-polysomal fractions between conditions individually (migrating in the same density) or in a pool;
3. non-polysomal to polysomal between conditions and within each condition individually (migrating in the same density) or in a pool; and
4. each of the fractions being polysomal and non-polysomal individually (migrating in the same density) or in a pool that can be compared to total RNA, that is unfractionated.

The method described above for the identification of translationally regulated genes has a number of applications. A particular application for this method is its use for the detection of changes in the pattern of mRNA expression in cells/tissue associated with any physiological or pathological change. By comparing the translated versus untranslated mRNAs, the effect of the physiological or pathological cue or stress on the change of the pattern of mRNA expression in the cell/tissue can be observed and/or detected. This method can be used to study the effects of a number of cues, stimuli, or stressors to ascertain their effect or contribution to various physiological and pathological activities of the cell/tissue. In particular, the present method can be used to analyze the results of the administrations of pharmaceuticals (drugs) or other chemicals to an individual by comparing the mRNA pattern of a tissue before and after the administration of the drug or chemical. This analysis allows for the identification of drugs, chemicals, or other stimuli which affect cells/tissue at the level of translational regulation. Utilizing this method, it is possible to ascertain if particular mRNA species are involved in particular physiological or disease states and, in particular, to ascertain the specific cells/tissue wherein the external stimulus, i.e., a drug, affects a gene which is regulated at the translational level.

A further embodiment of the present invention provides a method for identifying gene sequences coding for internal ribosome entry sites (IRES) and includes the general steps of inhibiting 5' cap-dependant mRNA translation in a cell, collecting a pool of mRNA from the cells, and differentially analyzing the pool of mRNA to identify genes with sequences coding for internal ribosome entry sites.

As described above, it is known that an exception to the standard 5'-cap dependent translation initiation exists. Sequences exist within untranslated regions (UTRs) of RNAs which can include the presence of specific sequences known as internal ribosome entry sites (IRES). (Ehrenfeld, 1996) These internal ribosome entry sites have been shown to support translation initiation for several prokaryotic and eukaryotic systems as set forth above. However, in order to identify translationally controlled genes via 5'-cap independent translation mechanisms and their association with both normal and abnormal processes, it is necessary to inhibit 5'-cap initiated translation so that 5'-cap independent mRNA translation can be selected for. This inhibition is necessary since IRES sequences are difficult, if not impossible, to identify by sequence homology.

In order to inhibit 5'-cap dependent translation and thereby select for the presence of 5'-cap independent translation, cells or tissues which are to be analyzed for the presence of internal ribosome entry sites must be treated in some manner to prevent or discourage the 5'-cap translation initiation mechanism. The mechanism(s) of standard scanning-type translation initiation should be substantially, if not totally, turned off or shut down to, in essence, shift the translation equilibrium in favor of IRES initiated translation. That is, recognition of the 5'-cap structure is inhibited by disrupting the normal mechanism for 5'-cap mediated initiation. The mechanism for inhibiting the 5'-cap translation can include any known means or mechanisms for preventing the initiation of 5'-cap mediated translation. One such mechanism for inhibiting 5'-cap mediated translation is the expression of Polio virus 2A protease into a cell, cell system, or tissue to be analyzed for the presence of IRES sequences. The use of the Polio virus 2A protease inhibits 5'-cap-dependent mRNA translation by inactivating the cellular 5'-cap-dependent translation machinery. This enables the identification of cellular IRES containing genes which may be translationally controlled and play a critical role in the immediate response of the cell following the application of a stress inducing element/stressor such as heat shock, hypoxia, or other stress inducing elements as set forth above, prior to gene activation. The Polio virus 2A protease prevents 5'-cap-mediated translation by cleaving the large subunit of eIF-4γ (p220) of eukaryotic translation initiation factor 4 (eIF-4) which is involved in the recognition of the mRNA 5'-cap.

In order to inhibit the 5'-cap-mediated translation, the Polio virus 2A protease must be incorporated into the cell or cells being analyzed for the presence of gene sequences coding for internal ribosome entry sites and/or for identifying translationally regulated genes. One such method for incorporating the Polio virus 2A protease into a cell involves the transformation of a target cell with an expression vector containing the gene which codes for the Polio virus 2A protease. Because the Polio virus 2A protease is deleterious to living cells when it is constituitively expressed, the expression vector containing the Polio virus 2A protease gene is coupled with a bacterial LacI inducible system wherein a LacI repressor is constituitively expressed under a CMV promoter. The Polio virus 2A protease may be expressed under a number of suitable promoters including the RSV, the TK, or the mini-TK promoter coupled at their 3' end to the LacI repressor binding sites. By transforming the target cells with an expression vector containing the LacI repressor and the Polio virus 2A expression vector, the expression of the Polio virus 2A protease can be induced upon treatment of the cells with isopropyl-β-D-thiogalatopyranoside (IPTG). Treatment of the target cells with IPTG relieves the binding of the LacI repressor molecules bound at the repressor binding sites thus enabling transcription of the Polio virus 2A protease. By coupling the expression of the Polio virus 2A protease to an inducible system, such as the LacI system, this mechanism allows for the establishment of control of the expression of the gene coding for the Polio virus 2A protease.

Examples of an embodiment of the present invention for identifying gene sequences coating for internal ribosome entry sites are set forth below in the examples.

Following induction of the expression of the Polio virus 2A protease in the target cells, RNA, presumably containing internal ribosome entry sites, can be collected and analyzed utilizing the methods described above to identify genes whose translation is up-regulated by the effects of the Polio virus 2A protease.

EXPERIMENTAL

Differential Translation
Materials and Methods
Preparation of cell extracts

Cells were centrifuged. The pellet was washed with PBS and recentrifuged. The cells were resuspended in 4× of one packed cell volume (PCV) with hypotonic lysis buffer (HLB: 20 mM TrisHCL pH=7.4; 10 mM NaCl; 3 mM $MgCl_2$). The cells were incubated five minutes on ice. 1×PCV of HLB containing 1.2% Triton X-100 and 0.2 M sucrose was added. The cells were homogenized with a Dounce homogenizer (five strokes with B pestle). The cell lysate was centrifuged at 2300 g for ten minutes at 4° C. The supernatant was transferred to a new tube. HLB containing 10 mg/ml heparin was added to a final concentration of 1 mg/ml heparin. NaCl was added to a final concentration of 0.15 M. The supernatent was frozen at −70° C. after quick freezing in liquid $N_2$ or used immediately.

Sucrose gradient fractionation

A linear sucrose gradient from 0.5M to 1.5M sucrose in HLB was prepared. Polyallomer tubes (14×89 mm) were used. 0.5 to 1.0 ml of cell extract was loaded on the gradient. The cells were centrifuged at 36,000 RPM for 110 minutes at 4° C. An ISCO Density Fractionator was used to collect the fractions and record the absorbance profile.

RNA purification

SDS was added to 0.5% and Proteinase K to 0.1 mg/ml and incubated at 37° C. for 30 minutes. Extract with an equal volume of phenol+chloroform (1:1). The aqueous phase was extracted with one volume of chloroform and the RNA was precipitated by adding Na-Acetate to 0.3M and 2.5 volumes of ethanol and incubating at −20° C. overnight. Centrifuged ten minutes, the supernatant was aspirated and the RNA pellet was dissolved in sterile, DEPC-treated water.

Differential analysis
Differential display:

Reverse transcription: 2 μg of RNA were annealed with 1 pmol of oligo dT primer $(dT)_{18}$ in a volume of 6.5 μl by heating to 70° C. for five minutes and cooling on ice. 2 μl reaction buffer (×5), 1 μl of 10 mM dNTP mix, and 0.5 μl of SuperScript II reverse transcriptase (GibcoBRL) was added. The reaction was carried for one hour at 42° C. The reaction was stopped by adding 70 μl TE (10 mM Tris pH=8; 0.1 mM EDTA). Oligonucleotides used for Differential display: The oligonucleotides were essentially those described in the Delta RNA Fingerprinting kit (Clonetech Labs. Inc.). There were 9 "T" oligonucleotides (SEQ ID Nos: 2–10) of the general sequence:

5' CATTATGCTGAGTGATATCTTTTTTTTTVV3(SEQ ID No: 1).

The 10 "P" oligonucleotides were of the general sequence:

5' ATTAACCCTCACTAAA "NNNNNNNNNN"3(SEQ ID No: 11)

where the 9 or 10 nucleotides between the quotes represent an arbitrary sequence and there are 10 different sequences (SEQ ID Nos: 12–21), one for each "P" oligo.

Amplification reactions: each reaction is done in 20 μl and contains 50 μM dNTP mix, 1 μM from each primer, 1× polymerase buffer, 1 unit expand Polymerase (Beohringer Mannheim), 2 μCi [α-$^{32}$P]dATP and 1 μl cDNA template. Cycling, conditions were: three minutes at 95° C., then three cycles of two minutes at 94° C., five minutes at 40° C., five minutes at 68° C. This was followed by 27 cycles of one minute at 94° C., two minutes at 60° C., two minutes at 68° C. Reactions were terminated by a seven minute incubation at 68° C. and addition of 20 μl sequencing stop solution (95% formamide, 10 mM NaOH, 0.025% bromophenol blue, 0.025% xylene cyanol).

Gel analysis: 3–4 μl were loaded onto a 5% sequencing polyacrylamide gel and samples were electrophoresed at 2000 volts/40 milliamperes until the slow dye (xylene cyanol) was about 2 cm from the bottom. The gel was transferred to a filter paper, dryed under vacuum and exposed to x-ray film.

Recovery of differential bands: bands showing any a differential between the various pools were excised out of the dried gel and placed in a microcentrifuge tube. 50μl of sterile H$_2$O were added and the tubes heated to 100° C. for five minutes. 1 μl was added to a 49 μl PCR reaction using the same primers used for the differential display and the samples were amplified for 30 cycles of: one minute at 94° C., one minute at 60° C. and one minute at 68° C. 10 μl was analyzed on agarose gel to visualize and confirm successful amplification.

Representational difference analysis

Reverse transcription: as above but with 2 μg polyA+ selected mRNA. Preparation of double stranded cDNA: cDNA from previous step was treated with alkali to remove the mRNA, precipitated and dissolved in 20 μl H$_2$O. 5 μl buffer, 2μl 10 mM dATP, H$_2$O to 48 μl and 2 μl terminal deoxynucleotide transferase (TdT) were added. The reaction was incubated 2–4 hours at 37° C. 5 μl oligo dT (1 g/μl) was added and incubated at 60° C. for 5 minutes. 5 μl 200 mM DTT, 10 μl 10× section buffer (100 mM Mg Cl$_2$, 900 mM Hepes, pH 6.6) 16 μl dNTPs (1 mM), and 16 U of Klenow were added and the mixture was incubated overnight at room temperature to generate ds cDNA. 100 μl TE was added and extracted with phenol/chloroform. The DNA was precipitated and dissolved in 50 μl H$_2$O.

Generation of representations: cDNA with DpnII was digested by adding 3 μl DpnII reaction buffer 20 V and DpnII to 25 μl cDNA and incubated five hours at 37° C. 50 μl TE was added and extracted with phenol/chloroform. cDNA was precipitated and dissolved to a concentration of 10 ng/tl. The following oligonucleotides are used in this procedure:

| | | |
|---|---|---|
| R-Bg1-12 5' GATCTGCGGTGA 3' | (SEQ ID No: 22) |
| | (SEQ ID No: 23) |
| R-Bg1-24 5' AGCACTCTCCAGCCTCTCACCGCA 3' | |
| J-Bg1-12 5' GATCTGTTCATG 3' | (SEQ ID No: 24) |
| | (SEQ ID No: 25) |
| J-Bg1-24 5' ACCGACGTCGACTATCCATGAACA 3' | |
| N-Bg1-12 5' GATCTTCCCTCG 3' | (SEQ ID No: 26) |
| | (SEQ ID No: 27) |
| N-Bg1-24 5' AGGCAACTGTGCTATCCGAGGGAA 3' | |

R-Bg1—12 and R-Bg1–24 oligos were ligated to Tester and Driver: 1.2 μg DpnII digested cDNA. 4 μl from each oligo and 5 μl ligation buffer ×10 and annealed at 60° C. for ten minutes. 2 μl ligase was added and incubated overnight at 16° C. The ligation mixture was diluted by adding 140 μl TE. Amplification was carried out in a volume of 200 μl using R-Bg1–24 primer and 2 μl ligation product and repeated in twenty tubes for each sample. Before adding Taq DNA polymerase, the tubes were heated to 72° C. for three minutes. PCR conditions were as follows: five minutes at 72° C., twenty cycles of one minute at 95° C. and three minutes at 72° C., followed by ten minutes at 72° C.

Every four reactions were combined, extracted with phenol/chloroform and precipitated. Amplified DNA was dissolved to a concentration of 0.5 μl and all samples were pooled.

Subtraction: Tester DNA (20 μg) was digested with DpnII as above and separated on a 1.2% agarous gel. The DNA was extracted from the gel and 2 μg was ligated to J-Bg1–12 and J-Bg124 oligos as described above for the R-oligos. The ligated Tester DNA was diluted to 10 ng/μl with TE. Driver DNA was digested with DpnII and repurified to a final concentration of 0.5 μg/μl. Mix 40 μg of Driver DNA with 0.4 μg of Tester DNA. Extraction was carried out with phenol/chloroform and precipitated using two washs with 70% ethanol, resuspended DNA in 4 μl of 30 mM EPPS pH=8.0, 3 mM EDTA and overlayed with 35 μl mineral oil. Denatured at 98° C. for five minutes, cool to 67° C. and 1 μl of 5M NaCl was added to the DNA. Incubated at 67° C. for twenty hours. Diluted DNA by adding 400 μl TE.

Amplification: Amplification of subtracted DNA in a final volume of 200 μl as follows: Buffer, nucleotides and 20 μl of the diluted DNA were added, heated to 72° C., and Taq DNA polymerase was added. Incubated at 72° C. for five minutes and added J-Bg1–24 oligo. Ten cycles of one minute at 95° C., three minutes at 70° C. were performed. Incubated ten minutes at 72° C. The amplification was repeated in four separate tubes. The amplified DNA was extracted with phenol/chloroform, precipitated and all four tubes were combined in 40 μl 0.2×TE, Digested with Mung Bean Nuclease as follows: To 20 μl DNA 4 μl buffer, 14 μl H$_2$O and 2 μl Mung Bean Nuclease (10 units/μl) was added. Incubated at 30° C. for thirty-five minutes+First Differential Product (DPI).

Repeat subtraction hybridization and PCR amplification at driver: differential ratio of 1:400 (DPII) and 1:40,000 (DPIII) using N-Bg1 oligonucleotides and J-Bg1 oligonucleotides, respectively. Differential products were cloned into a Bluescript vector at the BAM HI site for analysis of the individual clones.

Figure 2:
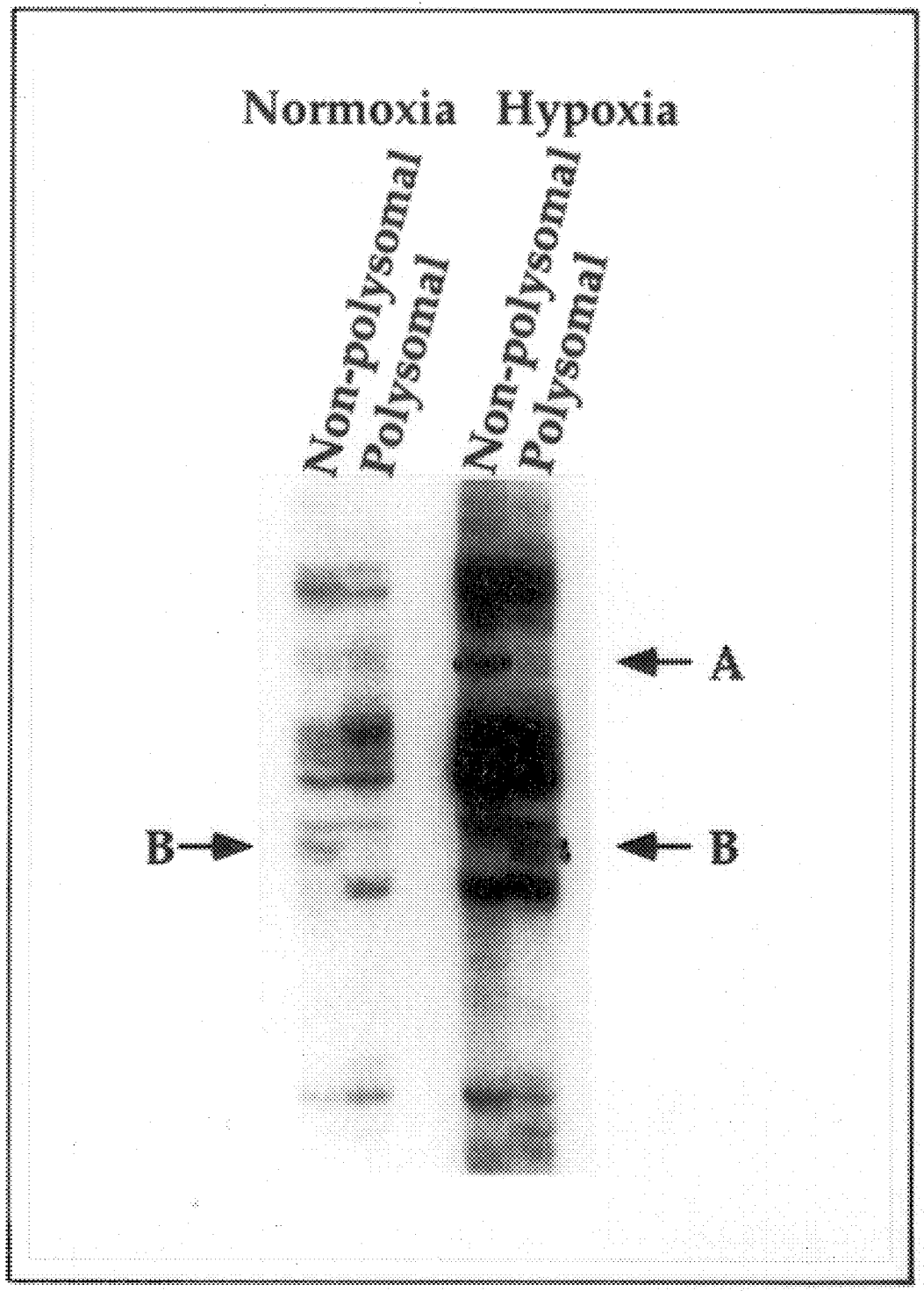
FIG. 2 is a photograph of a 5% acrylamide gel illustrating a differential translation analysis of mRNA from sucrose density gradients according to the present invention.

EXAMPLE 1
Differential Translation Analysis of mRNA From Sucrose Density Gradients C6 glioma cells were grown under normal conditions (Normoxia) or under oxygen deprivation conditions (Hypoxia) for eight hours. The cells were then harvested and cytoplasmic extracts were applied onto sucrose gradients. RNA was extracted from the fractions obtained from the sucrose gradient and pooled into polysomal and non-polysomal samples. Following reverse transcription, the differential display technique was applied using the primers T1 and P10 as set forth in Table 2. The PCR products were separated on a 5% acrylamide sequencing gel. The gel was then dried and exposed to X-ray film. The results are shown in FIG. 2 wherein "A" shows an mRNA species apparent only in a non-polysomal fraction of cells after eight hours of hypoxia. This represents a potentially transciptionally induced mRNA species which was still translationally repressed but which could be actively transcribed after prolonged hypoxia. "B" represents an mRNA species found in the non-polysomal fraction of cells grown under normal oxygen levels which was transferred into the polysomal fraction following hypoxia.

The materials and methods were performed as set forth above. This example demonstrates the utility of the present invention for identifying translationally regulating genes which are regulated by a stress inducing element.

EXAMPLE 2

Figure 3A:
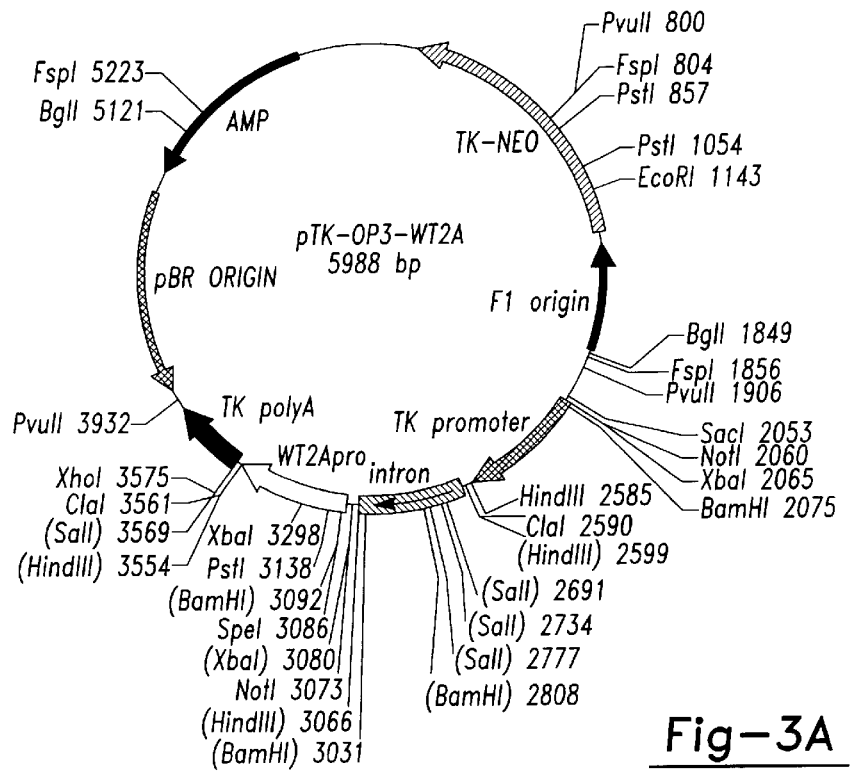
FIGS. 3A–C are schematic representations of plasmids that contain the Polio virus 2A genes (A) in plasmid pTK-OP3-WT2A, (B) in the plasmid miniTK-WT2A, and (C) in a plasmid containing a hygromycin selectable marker.
Figure 3B:
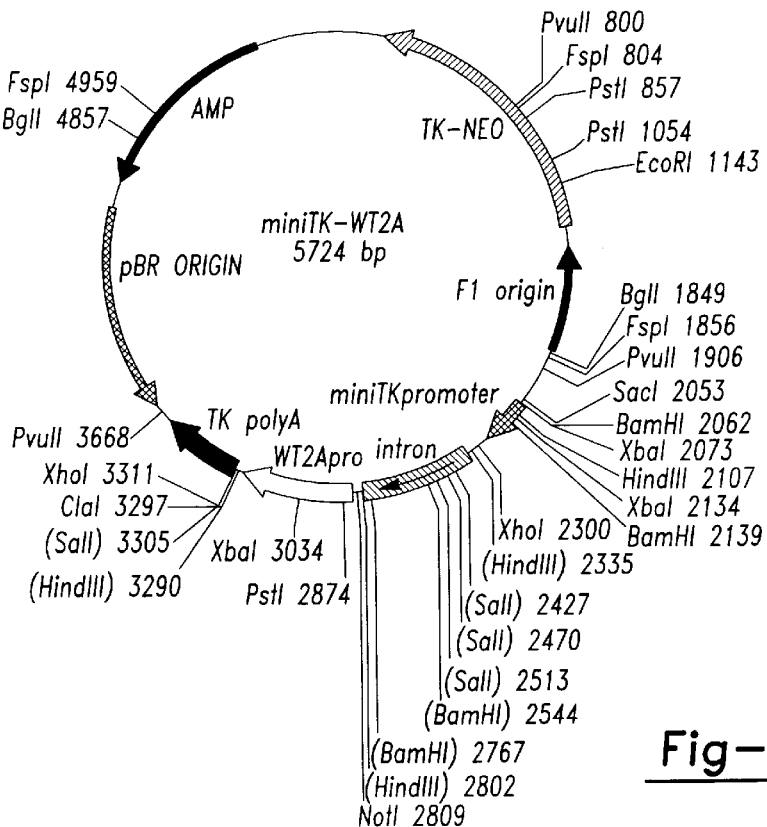
Figure 3C:
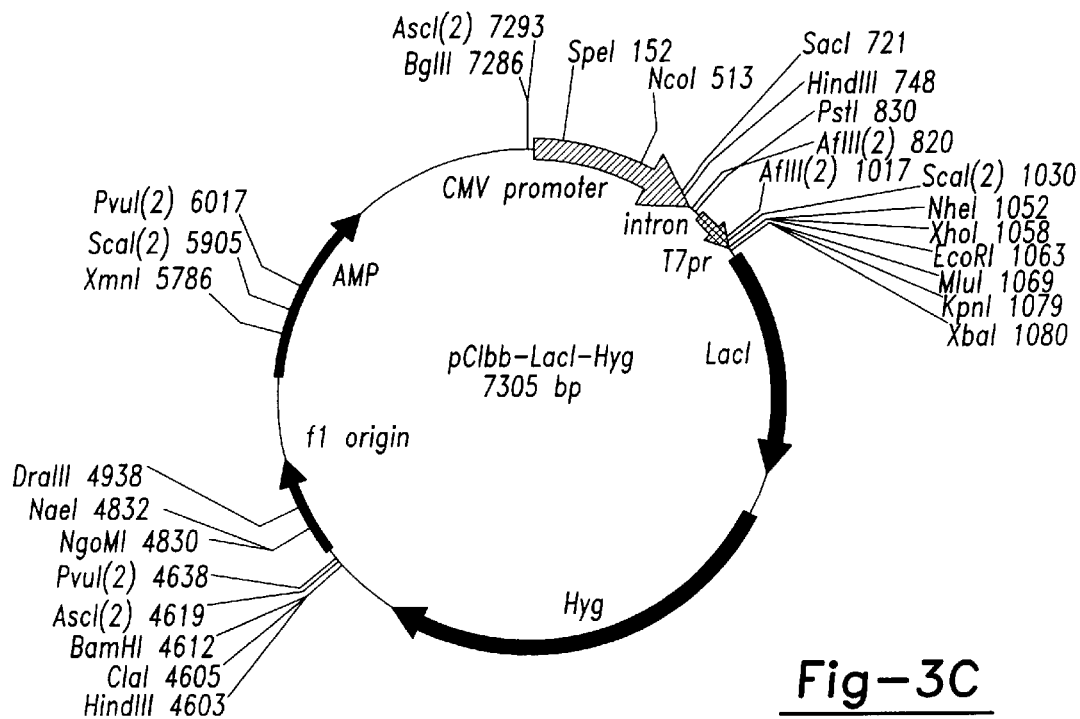

Identification of IRES Containing Genes
Establishment of mammalian cells expressing 2A protease HEK-293 human (ATCC CRI,-1573) cells were used as a model system for Polio virus 2A protease induced expression, since preliminary study indicated that 2A protease enhances expression of IRES containing genes in this cell line. HEK-293 cells were co-transfected with CMV-LacI—(constructed by applicant using techniques known to those skilled in the art) in combination with either one of the Polio virus 2A protease expression vectors PTK-OP3-WT2A, miniTK-WT2A, on PCIbb-LacI-Hyg (constructed by applicant on basis of vectors from Stratagene) as shown in FIGS. 3A–C, respectively. The LacI expression vector contained a hygromycin selectable marker, and the Polio virus 2A protease expression vector contained a neomycin selectable marker which enabled the isolation of clones resistant to both markers, presumably expressing both LacI repressor and Polio virus 2A proteins.

Analysis of Polio virus 2A protease expression

Figure 4:
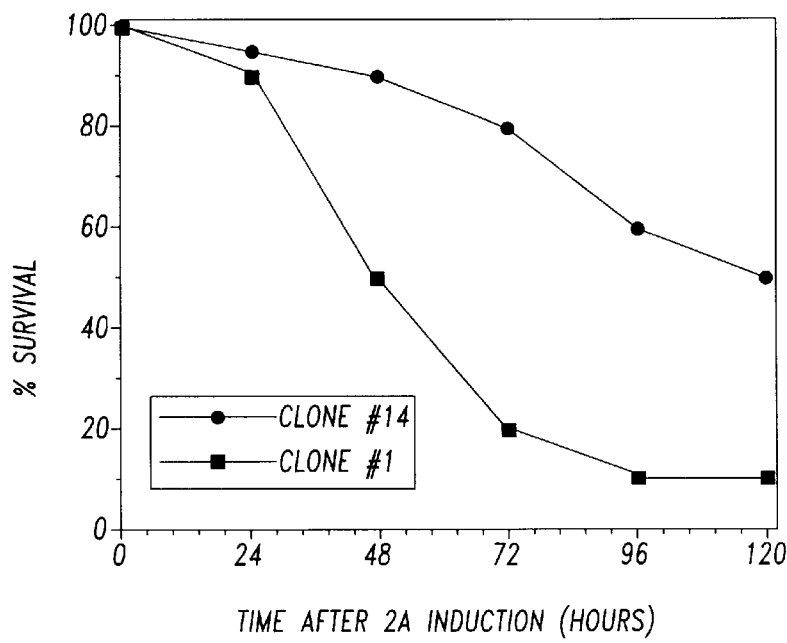
FIG. 4 is graph illustrating the induction of Polio virus 2A protease leading to cell death after induction of the 2A protease.

Death assay:—Resistant clones which grew after selection on hygromycin (50 μg/ml) and neomycin (500 μg/ml), were treated with IPTG (5 mM for 48 h+5 mM for further 48 h). Cells were then monitored for their viability and the clones that showed full mortality upon Polio virus 2A protease induction, presumably expressing the deleterious effect of the Polio virus 2A protease, were selected for further analysis. Two such clones were isolated, HEK-293 cells expressing Polio virus 2A protease under the control of a TK promotor (clone #14) and HEK-293 cells expressing the Polio virus 2A protease under the control of a miniTK promoter (clone #1) as shown in FIG. 4.

Analysis of 2A protease expression:—Direct analysis of the Polio virus 2A protease expression in HEK-293miniTK #1 clones and HEK-293TK #14 clones after IPTG induction was not performed due to the lack of antibodies against the protein. Several currently available techniques can be used to measure changes in gene expression including Northern blot analysis, RNase protection assay, in situ hybridization, and reverse transcriptase polymerase chain reaction (RT-PCR). RT-PCR is a very sensitive method, and was used to monitor the induction of the mRNA encoding for Polio virus 2A4 protease in HEK-293miniTK #1 clones following IPTG treatment. mRNA was prepared from HEK-293 parental cells and HEK-293miniTK-2A clones following treatment with IPTG at different time points. The RNAs were subjected to the RT-PCR reaction using Polio virus 2A protease specific oligonucleotides: 5'GCAACTACCATTTGGCCACTCAGGAAG3', (SEQ ID No: 28) and 5'GCAACCAACCCTTCTCCACCAGCAG3' and (SEQ ID No: 29).

Figure 5:
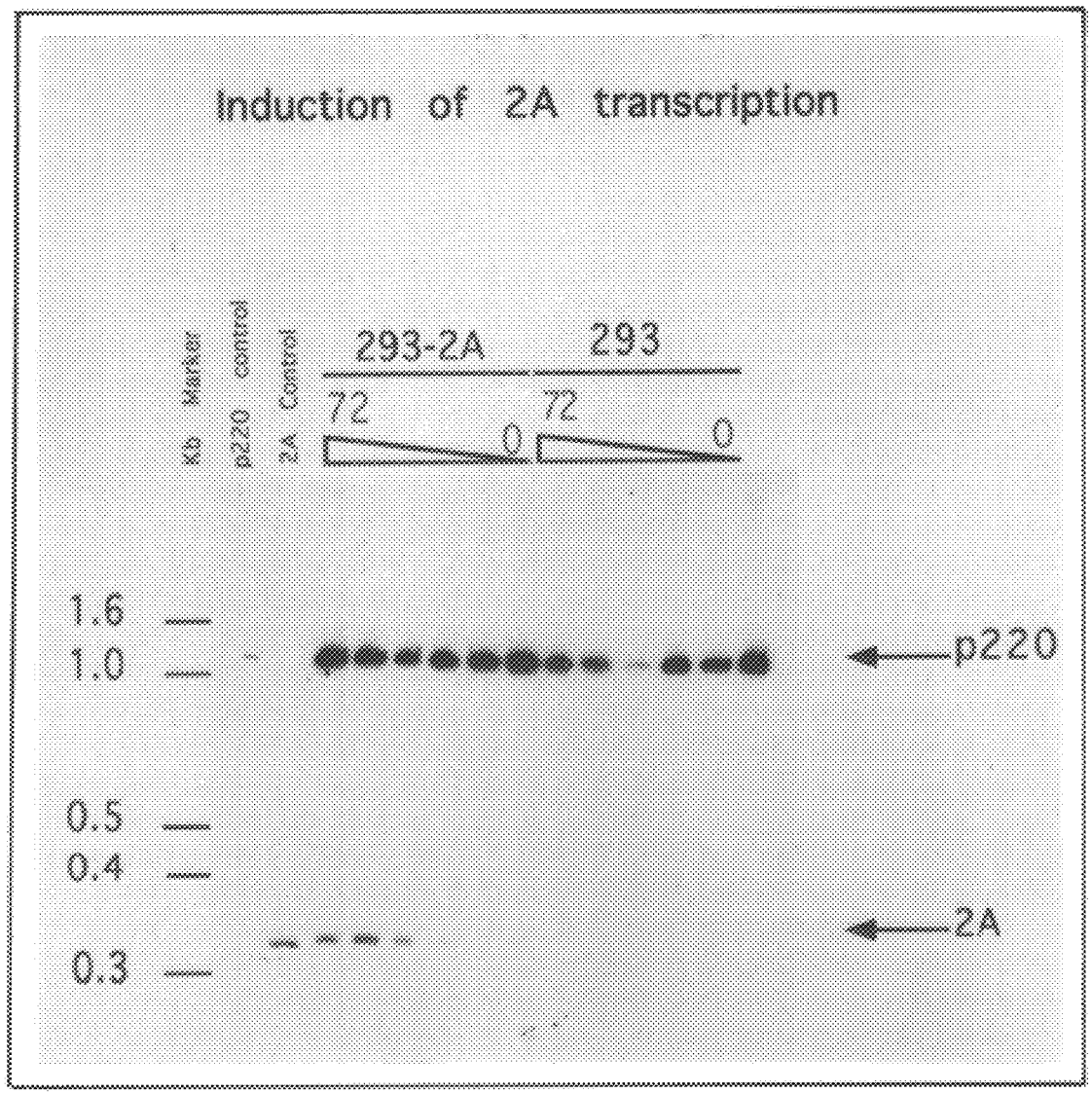
FIG. 5 is a photograph of a gel illustrating the presence of Polio virus 2A protease expression in transformed HEK-293 cells (293–2A) following induction with IPTG and the absence of the Polio virus 2A protease in HEK-293 (293) parental cells following treatment with IPTG.

Polio virus 2A protease mRNA was not detected in HEK-293 parental cells, however it was induced following IPTG treatment and reached its highest level after 48 hours of IPTG treatment as shown in FIG. 5.

Figure 6:
FIG. 6 is a photograph of a Western blot illustrating the activity of the Polio virus 2A protease in cleaving the p220 protein component of the 40S ribosomal subunit demonstrating that clones which were induced for Polio virus 2A protease generated cleavage products of the p220 protein.

Analysis of 2A protease activity p220 cleavage:—A well characterized function of Polio virus 2A protease is the cleavage of the p220 protein (4Fγ translational factor), a component of the 40S ribosomal subunit Cleavage of p220 yields three N-terminal cleavage products of 100–120 KDa molecular weight due to post-translational modification. p220 and its cleavage products were identified by 7% SDS PAGE and Western blot analysis using polyclonal anti-p220 antibodies specifically directed against the N-terminal region p220 as shown in FIG. 6. FIG. 6 demonstrates such an analysis in which HEK-293 miniTK2A #1 clone and HEK-293TK2A #14 clone were induced for Polio virus 2A protease expression to generate cleavage products of p220. As control, HEK-293 cell lysate was treated with Polio virus 2A protease produced by in vitro translation, and was found to generate identical cleavage products with the same mobility on 7% SDS PAGE as in the HEK-293 2A clones.

This system was used as the source of mRNA for polysomal fractionation. RDA analysis was performed using the protocol described above to identify genes whose translation was up-regulated by the effects of the Polio virus 2A protease. Table I summarizes the results of analyses performed according to the above-described method and genes isolated thereby.

TABLE 1

Translationally controlled genes are identified by the 2A protease system

A. Ribosomal proteins or proteins directly involved in translation encoded by mRNAs containing 5' TOP#
   S17      gbM13932
   S9       gb U14971
   EF-2     gbM19997
   L27a     gb U14968
   L37a     gbL06499
(Meyuhas et al., 1996)

B. Proteins encoded by mRNAs containing 5'TOP in their 5' UTR
   Laminin    binding receptor
   β1-tubulin   gb J00314

C. Gene with GC rich 5'UTR that regulates their translation
   spermidine synthase gbM34338
   retinol binding protein 5'UTR X00129

D. Unknown genes potenialy regulated by translation
   EST gb1059051   EST gb AA043162   EST gbW76915
   EST gbT54424    EST gb AA025896   D45282

TABLE 1-continued

Translationally controlled genes
are identified by the 2A protease system

EST gbH15523   EST gb R07358
EST gbW95821   EST gb H83477
EST gbW99369   EST T34436

E. Known genes that are potentially regulated by
translation (and may conatin IRES in their 5' UTR)
mitochondrial hinge protein gbS61826
gp25L2 mitochondrial protein gp25L2
mRNA encoding a protein related to lysyl t-RNA
synthetase emb z31711
SAP14 human splicesosome gb U41371

TABLE 2

Primers used in Differential Display Analysis

T Primers:

5'

| | | |
|---|---|---|
| T1: | CATTATGCTGAGTGATATCTTTTTTTTAA | (SEQ ID No: 2) |
| T2: | CATTATGCTGAGTGATATCTTTTTTTTAC | (SEQ ID No: 3) |
| T3: | CATTATGCTGAGTGATATCTTTTTTTTAG | (SEQ ID No: 4) |
| T4: | CATTATGCTGAGTGATATCTTTTTTTTCA | (SEQ ID No: 5) |
| T5: | CATTATGCTGAGTGATATCTTTTTTTTCC | (SEQ ID No: 6) |
| T6: | CATTATGCTGAGTGATATCTTTTTTTTCG | (SEQ ID No: 7) |
| T7: | CATTATGCTGAGTGATATCTTTTTTTTGA | (SEQ ID No: 8) |
| T8: | CATTATGCTGAGTGATATCTTTTTTTTGC | (SEQ ID No: 9) |
| T9: | CATTATGCTGAGTGATATCTTTTTTTTGG | (SEQ ID No: 10) |

P Primers:

| | | |
|---|---|---|
| P1: | ATTAACCCTCACTAAATGCTGGGGA | (SEQ ID No: 12) |
| P2: | ATTAACCCTCACTAAATGCTGGAGG | (SEQ ID No: 13) |
| P3: | ATTAACCCTCACTAAATGCTGGTAG | (SEQ ID No: 14) |
| P4: | ATTAACCCTCACTAAATGCTGGTAG | (SEQ ID No: 15) |
| P5: | ATTAACCCTCACTAAAGATCTGACTG | (SEQ ID No: 16) |
| P6: | ATTAACCCTCACTAAATGCTGGGTG | (SEQ ID No: 17) |
| P7: | ATTAACCCTCACTAAATGCTGTATG | (SEQ ID No: 18) |
| P8: | ATTAACCCTCACTAAATGGAGCTGG | (SEQ ID No: 19) |
| P9: | ATTAACCCTCACTAAATGTGGCAGG | (SEQ ID No: 20) |
| P10 | ATTAACCCTCACTAAATGCACCGTCC | (SEQ ID No: 21) |

Throughout this application various publications are referenced by citation and number. Full citations for the publication are listed below. The disclosure of these publications in their entireties are hereby incorporated by reference into this application in order to more fully describe the state of the art to which this invention pertains.

The invention has been described in an illustrative manner, and it is to be understood the terminology used is intended to be in the nature of description rather than of limitation.

Obviously, many modifications and variations of the present invention are possible in light of the above teachings. Therefore, it is to be understood that within the scope of the appended claims, the invention may be practiced otherwise than as specifically described.

REFERENCES CITED

Aiello et al., "Identification of multiple genes in bovine retinal pericytes altered by exposure to elevated levels of glucose by using mRNA differential display" *Proc. Natl. Acad. Sci. USA* Vol. 91, pp. 6231–6235 (1994).

Bauer et al., "Identification of differentially expressed mRNA species by an improved display technique (DDRT-PCR)" *Nucleic Acids Research,* Vol. 21,No. 18 (1993).

Bharucha and Ven Murthy., "Characterization of Polysomes and Polysomal mRNAs by Sucrose Density Gradient Centrifugation Followed by Immobilization in Polyacrylamide Gel Matrix" *Methods in Enzymology,* Vol. 216, pp. 168–179 (1992).

Braun et al., "Identification of Target Genes for the Ewing's Sarcoma EWS/FLI Fusion Protein by Representational Difference Analysis" *Molecular and Cellular Biology,* Vol. 15, No. 8, pp. 4623–4630 (1995).

Cold Springs Harbor Laboratory Press, Cold Spring Harbor, N.Y., 1989

Davis et al., Cell 51:987–1000, 1987.

Diatchenko et al., "Suppression subtractive hybridization: A method for generating differentially regulated or tissue-specific cDNA probes and libraries" *Proc. Natl Acad. Sci.,* Vol. 93, pp. 6025–6030 (1996).

Ehrenfeld, "Initiation of Translation by Picornavirus RNAs", *Translational Control* Cold Spring Harbor Laboratory Press, pp. 549–573, 1996.

Hadman et al., "Modification to the differential display technique reduce background and increase sensitivity" *Analytical Biochemistry* 226:383–386 (1995).

Hanauske-Abel et al., FEBS Letters 386 pp. 92–98 (1995).

Hirama et al., "Direct Purification of Polyadenylated RNAs from Isolated Polysome Fractions" *Analytical Biochemistry,* 155, pp. 385–390 (1986).

Hubank and Schatz, "Identifying differences in mRNA expression by representational difference analysis of cDNA" *Nucleic Acids Research.* Vol. 22, No. 25, p. 5640–5648 (1994).

Jefferies et al., "Elongation Faction-lot mRNA Is Selectively Translated following Mitogenic Stimulation" *The Journal of Biological Chemistry,* Vol. 269, No. 6, pp. 4367–4372 (1994).

Liang and Pardee, "Differential Display of Eukaryotic Messenger RNA by Means of the Polymerase Chain Reaction" *Science,* Vol. 257, pp. 967–971 (1992).

Liang et al., "Distribution and cloning of Eukaryotic mRNAs by means of differential display: refinements and optimization" *Nucleic Acids Research,* Vol. 21, No. 14, pp. 3269–3275 (1993).

Liang and Pardee, "Recent advances in differential display" *Current Opinion in Immunology,* 7:274–280 (1995).

Linskens et al., Cataloging altered gene expression in young and senescent cells using enhanced differential display" *Nuc. Ac. Res.* 23: 3244–3251 (1995).

Lisitsyn and Wigler, "Cloning the Differences Between Two Complex Genomes" *Science,* Vol. 259, pp. 946–951 (1993).

Mach et al., "Isolation of a cDNA Clone Encoding S-Adenosylmethionine Decarboxylase" *The Annual of Biological Chemistry,* Vol. 261, No. 25, pp. 11697–11703 (1986).

Macejak et al., "Internal inition of translation mediated by the 5' leader of a cellular mRNA" Nature, Vol. 353, pp. 990–94 (1991).

Mechler, "Isolation of messenger RNA from Membrane-Bound Polysomes" *Methods in Enzymology,* Vol. 152, pp. 241–253 (1987).

Menaker et al., "A Method for the Isolation of Rat Submandibular Salivary Gland Polysomes on Linear Sucrose Density Gradients" *Analytical Biochemistry* 57, pp. 325–335 (1974).

Meyuhas et al., "Translational Control of Ribosomal Protein mRNAs in Eukaryotes" *Translational Control,* pp. 363–388 (1996).

Mountford et al., "Internal ribosome entry sites and dicistronic RNAs in mammalian transgenesis" *TIG,* Vol. 11. No. 5, pp. 179–184 (1995).

Ogishima et al., "Fractionation of Mammalian Tissue mRNAs by High-Performance Gel Filtration Chromatography" *Analytical Biochemistry,* 138, pp. 309–313 (1984).

Oh et al., "Gene regulation: translational initiation by internal ribosome binding" *Current Opinion in Genetics and development,* pp. 295–300 (1993).

Pelletier et al., "Internal initiation of translation of eukaryotic mRNA directed by a sequence derived from poliovirus RNA" *Nature,* =l Vol. 334, pp. 320–325 (1988).

Schena et al., "Quantitative Monitoring of Gene Expression Patterns with a Complementary DNA Microarray" *Science,* Vol. 270, pp. 467–470 1995).

Shen et al., "Identification of the Human Prostatic Carcinoma Oncogene PTI-1 by Rapid Expression Cloning and Differential RNA Display" *Proc. Natl. Acad. Sci. USA,* Vol. 92, pp. 6778–6782 (1995).

Vagner et al. "Alternative Translation of Human Fibroblast Growth Factor 2 mRNA Occurs by Internal Entry of Ribosomes" *Molecular and Cellular* Biology, Vol. 15, No. 1, pp. 35–44 (1995).

Welsh et al., "Arbitrary primed PCR fingerprinting of RNA", *Nuc. Ac. Res.* 20:4965–49,70 (1992).

Zhao et al., "New primer strategy improves precision of differential display" *Biotechniques* 18: 842–850 (1995).

---

What is claimed is:

1. A method for identifying genes which can be translationally regulated by a stress inducing element, said method comprising the steps of:

selectively stimulating translation of an unknown target mRNA with a stress inducing element, the target mRNA being part of a larger sample of mRNA;

dividing the sample of mRNA into pools of translated and untranslated mRNA; and differentially analyzing the pools of mRNA to identify genes translationally regulated in response to the stress inducing element.

2. A method as set forth in claim 1, wherein the stress inducing element is further defined as a stressor of unknown relationship to gene translation.

3. A method as set forth in claim 2, wherein the stress inducing element is a toxin.

4. A method as set forth in claim 2, wherein the stress inducing element is a chemical.

5. A method as set forth in claim 2, wherein the stress inducing element is a pharmaceutical.

6. A method as set forth in claim 2, wherein the stress inducing element is an electric current.

7. A method as set forth in claim 2, wherein the stress inducing element is a pathogen.

8. A method as set forth in claim 1, wherein said analyzing step is further defined as differential display analysis.

9. A method as set forth in claim 1, wherein said analyzing step is further defined as representational difference analysis.

10. A method as set forth in claim 1, wherein said analyzing step is further defined as performing a gene expression microarray.

11. A method as set forth in claim 1, including the further step of cloning genes identified as being translationally regulated.

12. A method as set forth in claim 1, wherein said step of stimulating translation is further defined as chemically treating the cells.

13. A method as set forth in claim 1, wherein said step of stimulating translation is further defined as irradiating the cells.

14. A method as set forth in claim 1, wherein said step of stimulating translation is further defined as depriving the cells of oxygen.

15. A method as set forth in claim 1, wherein the cells are stimulated to differentiate.

16. A method as set forth in claim 1, wherein the mRNA sample includes cells that have undergone different treatments to stimulate mRNA translation in at least one pool of mRNA.

17. A method as set forth in claim 1, wherein said analyzing step distinguishes between polysomal fractions that migrate in the same density on diffuse gradients or in a pool.

18. A method as set forth in claim 1, wherein said analyzing step distinguishes between nonpolysomal fractions individually or as a pool.

19. A method as set forth in claim 1, wherein said analyzing step distinguishes between stimulated polysomal and nonpolysomal fractions individually or in a pool.

20. A method as set forth in claim 1, wherein said analyzing step distinguishes between each of the polysomal and nonpolysomal fractions individually or in a pool compared to an unfractionated total RNA pool.

\* \* \* \* \*